United States Patent [19]

Van der Heiden et al.

[11] Patent Number: 4,997,430
[45] Date of Patent: Mar. 5, 1991

[54] METHOD OF AND APPARATUS FOR ADMINISTERING MEDICAMENT TO A PATIENT

[75] Inventors: Johannes Van der Heiden, Groningen; Frank T. Biekart; Hubertus E. Hilbrink, both of Emmen, all of Netherlands

[73] Assignee: NPBI Nederlands Produktielaboratorium Voor Bloedtransfusieapparatuur en Infusievloeistoffen B.V., Emmer-Compascuum, Netherlands

[21] Appl. No.: 403,744

[22] Filed: Sep. 6, 1989

[51] Int. Cl.$^5$ ............................................... A61J 1/00
[52] U.S. Cl. ................................... 604/414; 604/405; 604/126; 604/248
[58] Field of Search ............... 604/411, 412, 414, 413, 604/403, 405, 406, 416, 248, 126; 222/80-83

[56] References Cited

U.S. PATENT DOCUMENTS

| | | |
|---|---|---|
| 3,757,981 | 9/1973 | Harris, Sr. et al. .................. 604/414 |
| 3,938,520 | 2/1976 | Scislowicz et al. ................. 604/405 |
| 4,614,267 | 9/1986 | Larkin . |
| 4,759,756 | 7/1988 | Forman et al. . |
| 4,787,898 | 11/1988 | Raines .................................. 604/405 |
| 4,822,351 | 4/1989 | Purcell ................................ 604/414 |
| 4,857,068 | 8/1989 | Kahn ................................... 604/411 |

Primary Examiner—Stephen C. Pellegrino
Attorney, Agent, or Firm—Herbert Dubno

[57] ABSTRACT

An aseptic solution for IV administration is prepard by thrusting a drug vial over a needle of a connector having a valve provided with a sterilizing air filter. In a first position of the valve, the communication to the IV container is blocked, but the vial is connected to the atmosphere through the sterilizing air filter to allow equalization of the atmospheric pressure with the pressure in the vial. In the second position, the communication with the filter is cutoff and the vial is connected to the IV container to allow IV solution to enter the vial and solution to be transferred between the vial and the IV container. In a final position, the ports of the valve are all blocked to close off the vial in which the sterile air is now trapped so that loss of the IV solution into the vial will be prevented.

19 Claims, 5 Drawing Sheets

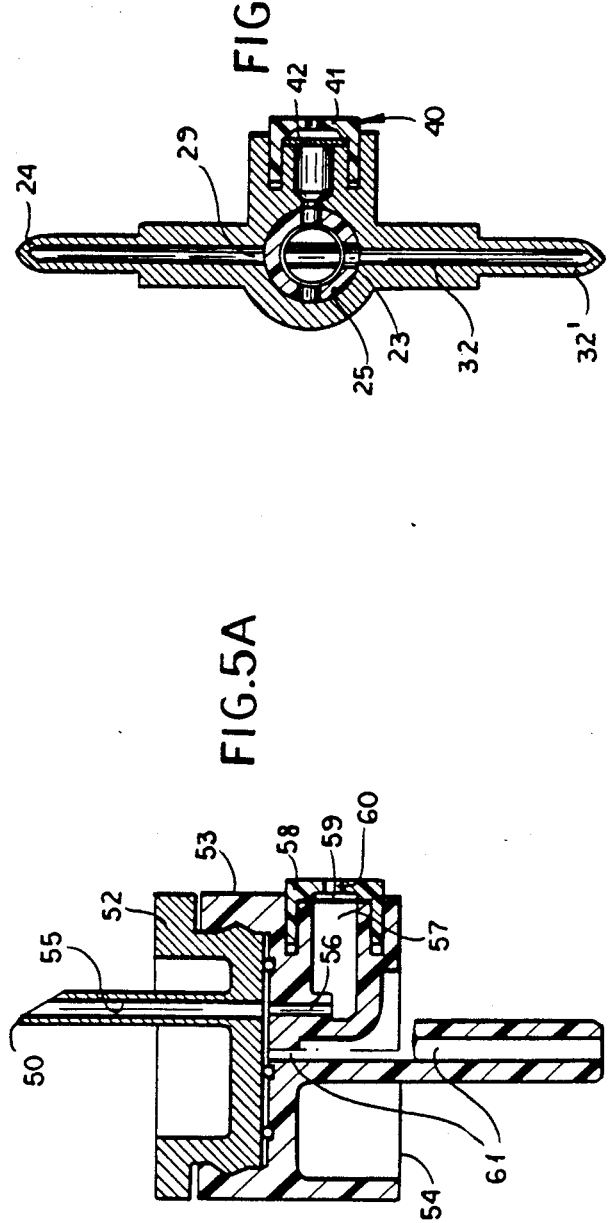
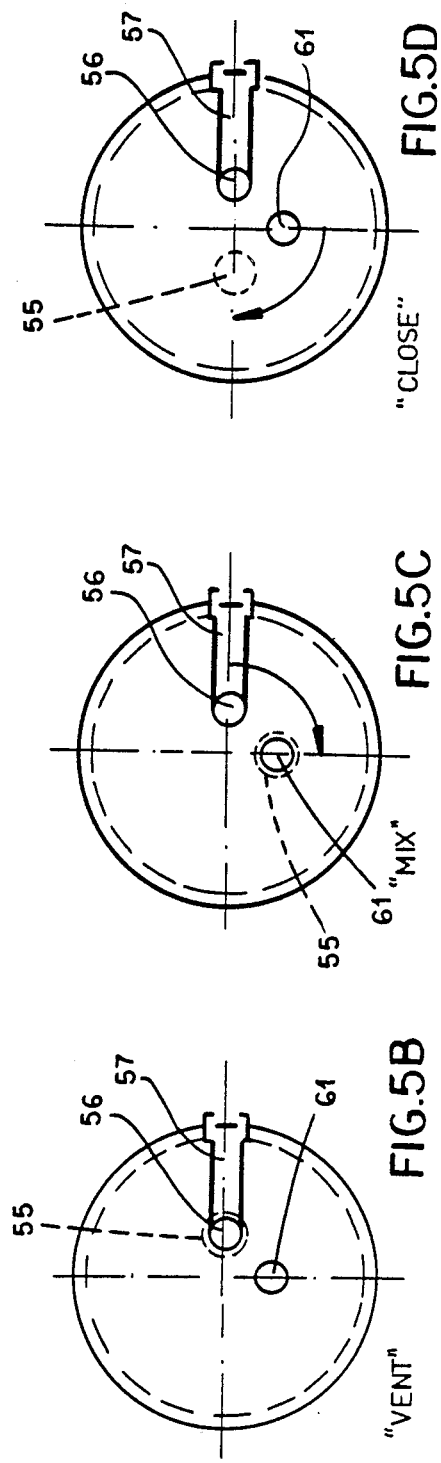

METHOD OF AND APPARATUS FOR ADMINISTERING MEDICAMENT TO A PATIENT

FIELD OF THE INVENTION

The present invention relates to a method of and to an apparatus for the administration of medicament to a patient and, more particularly, to an apparatus and connector which will allow a vial of a medicament to be admixed with a solution capable of administration to a patient by intravenous or other administration techniques.

BACKGROUND OF THE INVENTION

A preferred administration of many drugs utilizes continuous or intermittent intravenous infusion.

For such administration and, generally, for parenteral administration of many medicaments, it is important to dilute the drug or medicament with a biologically compatible solution or vehicle. While the present description will be confined largely to the preparation of intravenous administration media, it should be understood that the invention is applicable to other administration systems in which a vehicle is intended to carry the medicament into the body and a sterile admixture of the medicament to the vehicle is to take place.

The most commonly used intravenous solutions for this purpose are 5 percent dextrose and 0.9 percent sodium chloride solutions, the latter being generally referred to as physiological saline.

These solutions are available in glass bottles or flexible containers of different sizes or volumes from different manufacturers.

The solutions are packaged in glass bottles usually under a vacuum and, because the flexible containers respond to atmospheric pressure, the contents thereof generally are under atmospheric pressure or pressureless if the atmospheric pressure is considered to be the reference point for measurement.

The drugs which must be diluted with such solutions can be packaged in dry powdered form or in a liquid form in glass vials. The glass vials themselves derive from many different manufacturers and may differ in size, volume and the pressure within the vial depending upon the production process or the packaging process of the manufacturer.

For example, the pressure within the vial may range from a deep vacuum of about 0.9 bar to a slight overpressure. Many of these vials can have an aluminum cap as governed by international or local standards, for example ISO-DIS 8362-3, with a rubber stopper of either 20 mm or 13 mm in diameter and constituting a self-sealing membrane which can be penetrated by a needle.

The state of the art in preparing a powdered drug in an intravenous form is to first inject a portion of the diluent into the drug vial. Since the powdered form of the medicament may be in lyophilized form, this step is referred to as a reconstitution. For this purpose, the needle of a syringe is pierced through the rubber stopper of the drug vial and the diluent is introduced in the vial by the syringe. After mixing and dissolution of the powder in the liquid, the solution is drawn back into the syringe and may be injected by the syringe through an appropriate port in the container in which the intravenous medium has been packaged. After mixing of the syringe solution with the packaged solution, the packaged mixture can be administered to the patient.

The preparation of intravenous solutions in this manner may cause risk to the patient.

For example, microorganisms can be introduced which can cause thrombofiebitis and often fatal infection. Studies have indicated that 5 to 55 percent of intravenous solutions prepared in the above-described manner may be contaminated with microorganisms.

The chances of inadvertently introducing microorganisms into a solution increase with every step in the reconstitution and dilution process. It is important, therefore, to use a process having as few steps as is possible.

Mention may also be made of the fact that reconstitution and dilution processes may cause the introduction of pyrogens which can cause fever, particulate matter which can obstruct small arteries and veins and air which can cause the formation of lethal embolisms and can otherwise obstruct arteries and veins. The reconstitution or preparation of intravenous solutions can also be dangerous for the operator who performs the reconstitution or dilution. For example, the drug itself may be hazardous in the case of antineoplastics which are dangerous and hazardous even in small quantities when the exposure takes place over a period of time. Exposure to drugs through aerosols, needle leakage, drips and the like also may be hazardous. It is important, therefore, both for the patient and for the operator to be able to reconstitute the drug in an intravenous solution with a minimum number of steps, in a minimum amount of time and with a minimum danger of exposure of the operator to the diluted and nonreconstituted drug and to prevent inadvertent exposure of personnel to drugs while also preventing inadvertent introduction of foreign matter into the intravenous solution.

Several techniques have been developed to avoid problems of the type previously referred to. For example, a double-pointed needle has been developed. This needle, commonly known as a transfer needle, is pierced through the closure of the drug vial and then through the additive port of a flexible container or bag for the intravenous solution. The solution is forced from the container into the vial and then from the vial into the container by squeezing action. Any air that was in the container can then be forced into the vial. This technique and modifications thereof are described in U.S. Pat. No. 4,759,756.

In U.S. Pat. No. 4,614,267, a dedicated system is described in which the IV container and the drug vial are provided with mutually engaging means which secure the vial to the container. The vial can be screwed into the container and the rubber stopper can be removed to allow mixing of the IV solution the the drug.

Both of these systems are dependent on the presence of air. Air is needed, for example, to equalize the pressure of the total system with atmospheric pressure. In the absence of air, part of the reconstituted solution will remain trapped and will preclude complete delivery of a medicament dose to the patient. This can be detrimental.

In the case of transfer needles, the air comes from outside the system. When the drug vial is pierced with this needle, air is drawn into the drug vial and the pressure inside of the vial is equalized with atmospheric pressure. The advantage of this system is that the IV container can be essentially free from air. However, even if the reconstitution takes place in a sterile cabinet, there is always the danger of some contamination when the nonsterile air is introduced into the vial or from the vial into the IV solution.

In the system of U.S. Pat. No. 4,614,267, the air comes from within the system and IV containers for use in this system must, therefore, contain a certain volume of the air. This air is, of course, sterile and the sterility of the air is maintained. The system is not, however, satisfactory in many cases, because the amount of air required by the vial for suitable mixing will vary in accordance with the packaging pressure and the nature of the drug to be administered. For example, a vial with a vacuum of 0.9 bar and a volume of 100 ml will require 90 ml of air for atmospheric pressure balance while a vial packaged with a slight overpressure has to release air. Most drug vials fall somewhere within this range and it has been difficult to correlate the different vials with this latter system, especially where the system requires the use of proprietary vials under the control of a single licensor. Indeed, the IV containers for the latter system have generally had to have a large air volume to ensure equalization of pressure with the vials of the deepest vacuum and this may leave a volume of air in the container after reconstitution of 50 ml or more. The presence of any air can, of course, be detrimental to the organism because air introduced into the blood stream may occlude arteries and veins and cause tissue damage. It is generally thought that the introduction of 50 to 100 ml of air into the blood stream can be lethal.

Intravenous injection systems, therefore, must be carefully monitored for the presence of air and generally it is important to avoid the presence of any air in such systems.

OBJECTS OF THE INVENTION

It is, therefore, an important object of the present invention to provide an improved method of producing an infusion solution with a medicament whereby these drawbacks can be avoided and, in particular, the mixture of a medicament with an IV solution can be effected without substantial danger of the inclusion of air in the final product, but yet with vials packaged under a wide range of pressures or vacuums.

Another object of the invention is to provide a method of and an apparatus for preparing IV solutions and the like with reduced danger of inclusion in the administrable solution of foreign matter, namely, microorganisms, pyrogens and particles.

It is also an object of our present invention to provide an apparatus and connector for use between a drug vial and a flexible wall IV container which will simplify the preparation of an administrable solution while at the same time preventing exposure of the user to the medicament.

SUMMARY OF THE INVENTION

These objects and others which will become apparent hereinafter are attained, in accordance with the present invention, in a method of preparing an aseptic solution for administration which comprises the steps of:

(a) providing a flexible container containing a physiological diluent and having a valve formed with a piercing needle and a sterilizing filter communicating with the atmosphere;

(b) fitting a medicament vial over the needle whereby the needle pierces a sealing membrane of the vial;

(c) in a first position of the valve communicating between the filter and the vial and blocking communication of the container with the vial and the filter, admitting sterile air from the atmosphere through the filter into the vial to bring a pressure in the vial to atmospheric pressure;

(d) thereafter in a second position of the valve communicating between the vial and the container and blocking communication of the vial and the container with the filter, squeezing the container at least once to displace diluent from the container into the vial and a mixture of diluent and the medicament from the vial into the container; and (e) thereafter forcing air from the container into the vial.

The apparatus used for this purpose comprises:

a flexible container containing a physiological diluent;

a valved connector passing through a wall of the container and including:

a connector body formed with a piercing needle, a tubular stem insertable through the wall of the container, and means displaceable into a first position for connecting a port of the body to the needle, a second position for connecting the needle with the container and blocking communication with the port, and a third position blocking communication between the needle and the container and blocking communication between the port and the container;

a sterile filter on the connector communicating between the port and the atmosphere; and a vial having a sealing membrane pierceable by the needle and adapted to be received by the connector over the needle, whereby in the first position of the valve the filter communicates with the vial and communication of the container with the vial and the filter is blocked, and sterile air from the atmosphere is admitted through the filter into the vial to bring a pressure in the vial to atmospheric pressure, thereafter in the second position of the valve the vial communicates with the container and communication of the vial and the container with the filter is blocked so that squeezing the container at least once displaces diluent from the container into the vial and a mixture of diluent and the medicament from the vial into the container, and in the third position, mixture from the container is prevented from reentering the vial.

More specifically, the connector of this invention, attached to a flexible container containing a diluent for introducing the medicament into the container comprises:

a connector body;

a piercing needle on the body adapted to pierce a sealing membrane of a medicament vial;

means for connecting the connector body with the container;

a port formed in the body and a sterilizing filter connecting the port with the atmosphere; and means on the body displaceable between a first position wherein the port is connected with the needle and communication between the port and the container is blocked, and a second position wherein the needle is connected with the container and communication with the port is blocked.

The connector as described thus forms the critical feature of the invention in that, when fitted to the flexible container and having a medicament vial forced over its needle, it has a position providing an air path which equalizes the pressure in the drug vial with air drawn from the exterior via a sterilizing air filter forming part of the connector. The essential elements of the connector, therefore, are a tube which can be fitted into the infusion container, the valve structure itself, a sterilizing air filter and the piercing member or needle for the drug vial. The piercing member can be connected via the valve means to either the path provided with the air filter or the path communicating with the IV container. The valve has at least two different positions, namely, a "vent" position and a "mix" position.

In the "vent" position, the piercing member is connected to the air filter and sterile air can be admitted to the medicament vial to equalize the pressure therein with atmospheric pressure. In the "mix" position, the piercing member is connected to the interior of the IV solution container. In this position, the liquid in the container and the sterile air and contents of the vial can be exchanged. It is important to the present invention that in this position, there be no communication between the piercing member and the air filter and the container which may allow excess air to be drawn into the container.

The connector may be fitted with a ring permitting a tight fit between the connector and the drug vial so as to secure the vial to the connector and this ring can be provided with a skirt protecting the operator against leakage and splashing.

This ring can be an adaptor designed to accommodate standard vial heads. The connector can be fitted to the flexible IV container by the manufacturer and the container can be filled with the IV solution by the manufacturer so that it is not necessary to provide any excess air therein. The connector is simply placed over the mouth of the drug vial or the drug vial is pressed over the needle, thereby establishing communication between the piercing member and the interior of the vial through the rubber stopper of the vial.

The air filter on the connector can have a pore size of 0.3 micrometer or less, ensuring sterilization.

Generally, the improved valve of the invention will only be used in combination with the IV container. The manufacturer will make the connection between the container and the connector, sterilize this combination together and sell it already connected. By doing this, we avoid any potentially aseptic step of connecting the connector and the IV container under nonsterile conditions. However, we do not exclude the possibility that our valve can be used as an improved transfer needle. In an operation in which the valve is also a transfer needle, the valve provided with a needle in the place of the tubular stem for properly inserting it through a membrane in the IV container.

BRIEF DESCRIPTION OF THE DRAWING

The above objects, features and advantages of our invention will become more readily apparent from the following description, reference being made to the accompanying drawing in which:

FIG. 5A is a cross-sectional view through an embodiment of the valve;

FIGS. 5B-5D are diagrams showing the various positions of this valve; and

FIG. 6 is a view similar to FIG. 2A showing a transfer-needle embodiment of the invention.

SPECIFIC DESCRIPTION

Figure 1:
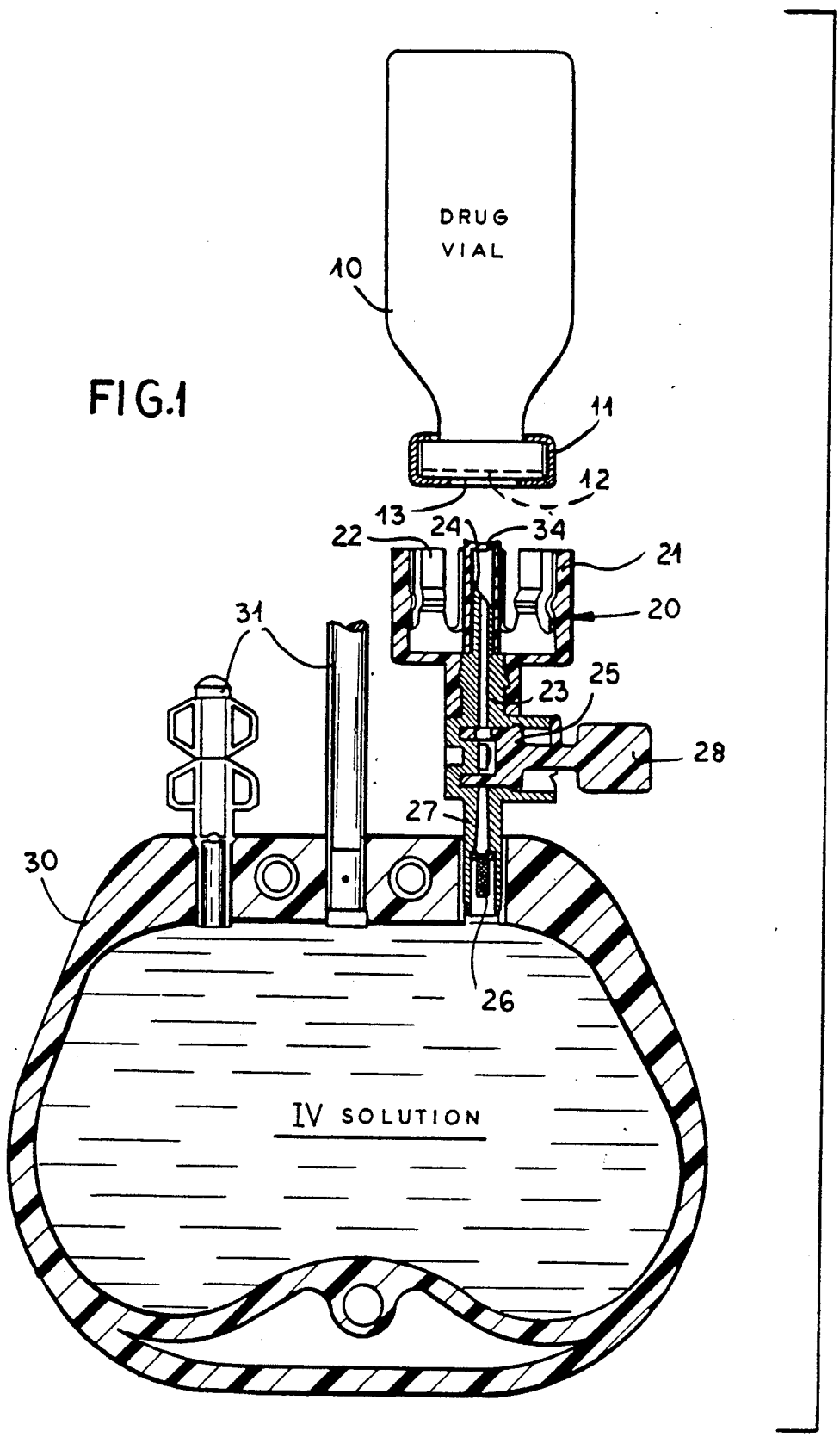
FIG. 1 is a cross-sectional view through the apparatus of the invention showing a drug vial in elevation about to be fitted into the adaptor.

Turning now to FIG. 1, it can be seen that a drug vial 10, which can contain a liquid or powdered medicament (not shown) can have a standardized cap 11 covering a rubber stopper or membrane 12 to which access is afforded through a window in the metal cap when, for example, a pulltab or protective cover is removed.

The drug vial 10 is adapted to fit into an adaptor 20 mounted upon a valve body 23 of the connector, the adaptor 20 having an apron 21 provided with resilient fingers 22 adapted to size the head of the vial to hold it in place.

A protective cap 34 fits like a sleeve over the needle 24 and can be removed before the drug vial is pressed into the adaptor. The needle 24, formed on the valve body 23, constitutes a piercing member as described.

A valve member 25 is provided, as will be described, to effect the successive connections in accordance with the invention. The valve member 25 has a handle 28 enabling it to be rotated easily by the operator.

A tube or stem 27 can have previously (upon manufacture) been fitted into the flexible container 30 for the IV solution and can have a filter 26 preventing particulates from entering the solution from the vial 10.

Turning now to FIGS. 2A-2D, it can be seen that the valve member 25 has three radial ports 25a, 25b, 25c all communicating with a chamber 25d of the valve member 25. The sterilizing air filter 40 communicates via a port 43 with the valve and can comprise a filter membrane 42 of a pore size of 0.3 micrometer or less, held in place by a cover 41.

The needle 24 has a needle passage 29 and the tube 27 has a passage 32 communicating with the container.

Figure 2D:
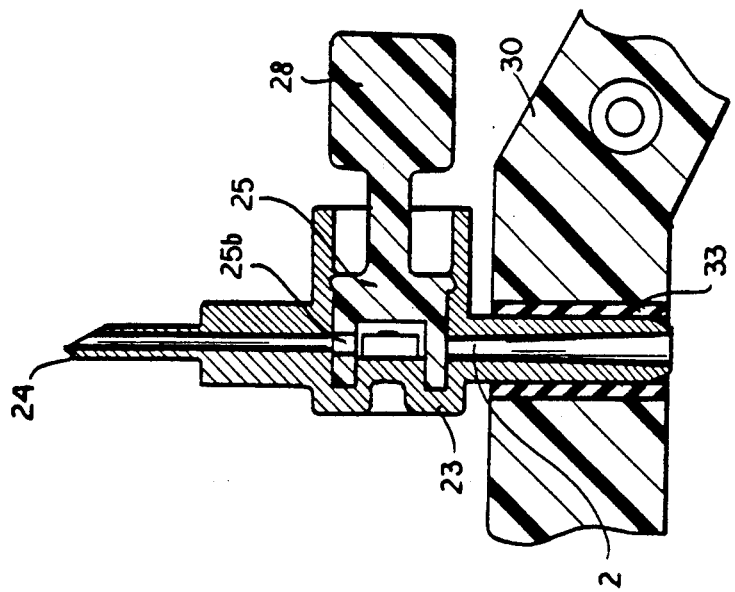
FIG. 2D is a cross-sectional view of a portion of the valve in its position shown in FIG. 2A.
Figure 2C:
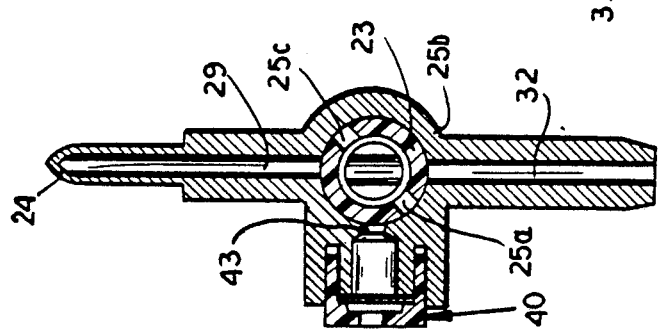
FIGS. 2A-2C are diagrammatic cross-sectional views through the valve structure of this apparatus showing different positions thereof.
Figure 2B:
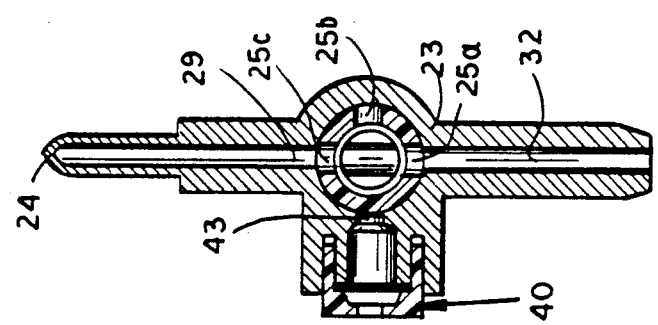
Figure 2A:
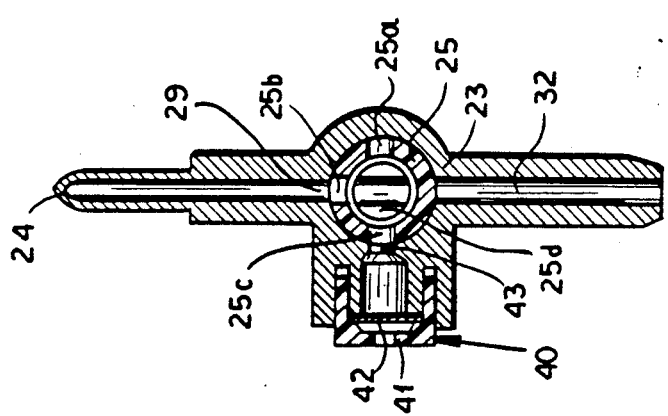

In the position shown in FIG. 2A, the bore 25b and the passage 29 register with one another, while the port 43 registers with the bore 25c. Accordingly, sterilizing filter 40 communicates with the needle 24 and the drug vial while communicating with the passage 32 and the interior of the container 30 is blocked. This is, of course, the "vent" position mentioned previously.

In the "mix" position shown in FIG. 2B, passage 29 communicates via bore 25c and bore 25a with the passage 32 while communication via port 43 with the air filter 40 is blocked. In a "close" position shown in FIG. 2C, passages 29, 32 and 43 are all blocked. The IV connector 30 can have other fittings 31, commonly required for administration of the IV.

The valve of FIGS. 2A-2C is normally connected to the IV container at the manufacture thereof. However, it can be provided with a second needle 32' to allow it to pierce a membrane of the container where this can be done under sterile conditions (see especially FIG. 6).

We can provide sterile docking to connect our valve with the IV container. This can be done by the operator in the hospital laboratory and will maintain sterility inside the container. We intend to, in this case, provide the IV container with a piece of tubing that is closed at one side and connected through the wall of the container at the other. The connector is also provided with a piece of tubing that is closed at one end and connected to the tubular stem at the other. Both pieces of tubing can be connected in a sterile manner by means of a sterile docking device such as is marketed by Heamonetics.

Figure 3A:
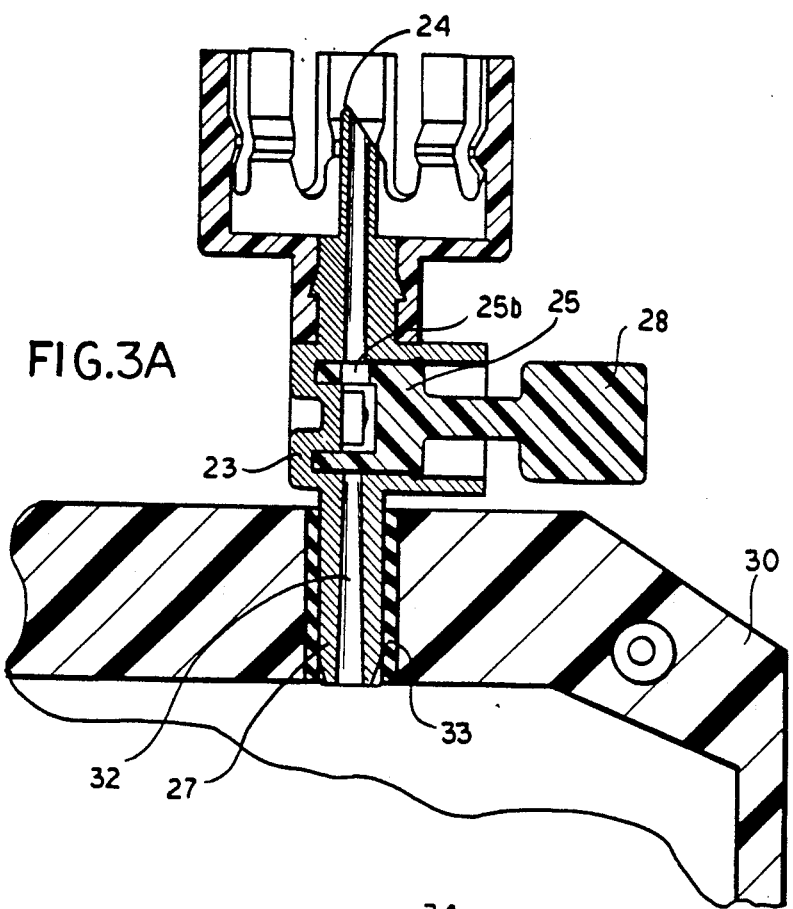
FIGS. 3A and 3B are cross-sectional views of two different embodiments of the connector of the invention.
Figure 3B:
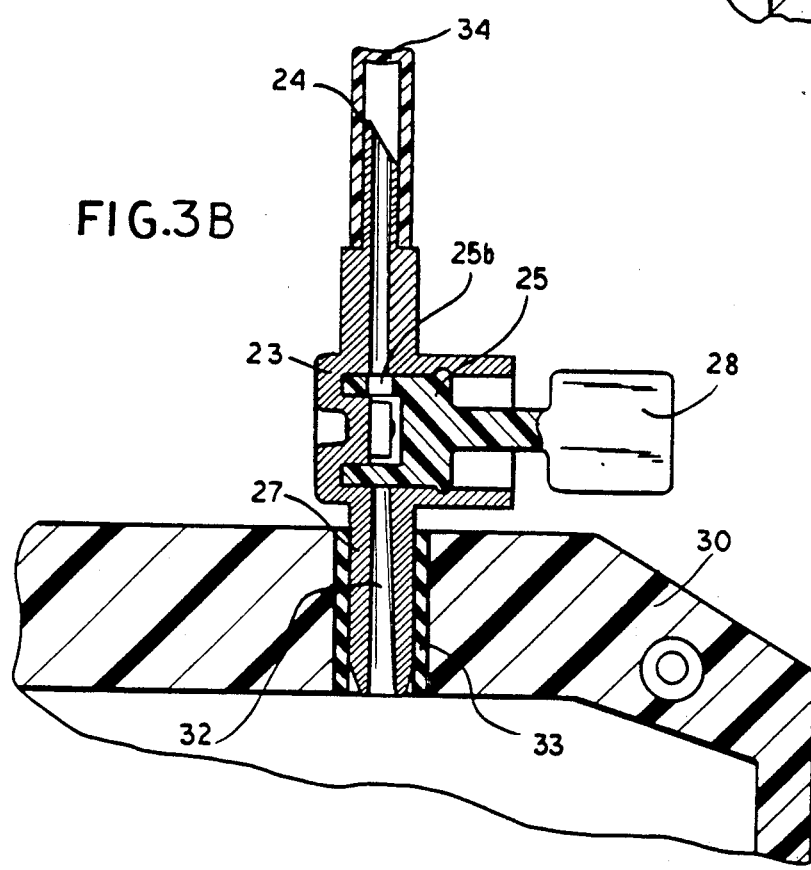

The construction of the connector is shown in greater detail in FIG. 3A. In FIG. 3B, we show a modified version of the connector in which the needle 24 is covered by the cap 34 but no adaptor forming a skirt around the vial is provided.

Figure 4A:
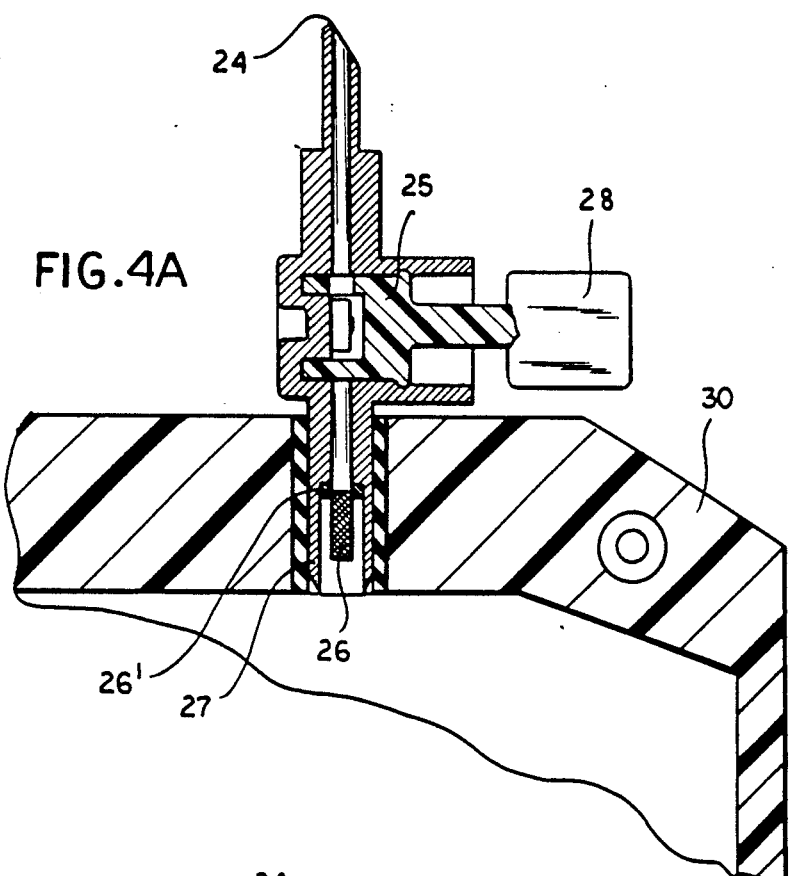
FIG. 4C is a perspective view of a portion of the valve of FIG. 4B.

As can be seen from FIG. 4A, the particulate filter 26 can be held in place by a ring 26' in the tube 27 two prevent particulates from entering the IV connector.

Figure 4B:
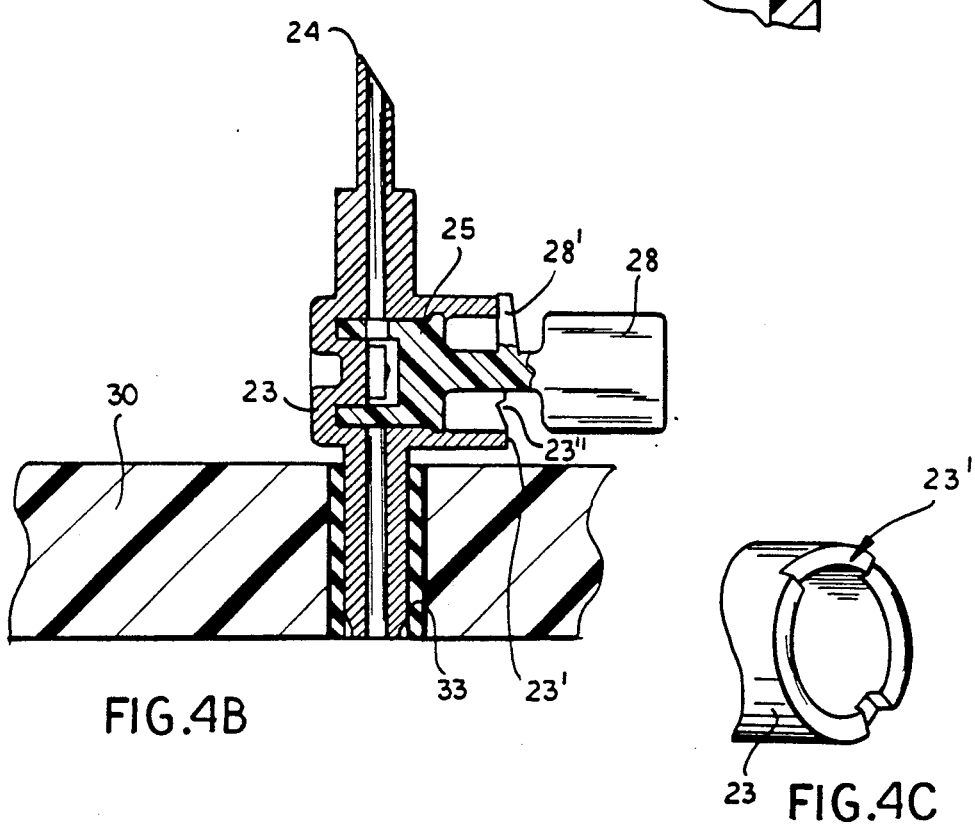
Figure 4C:
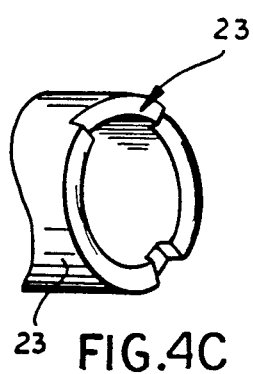

FIG. 4B shows the valve 25 can be provided with a unidirectional mechanism allowing rotation of the valve 25 through the positions shown in FIGS. 2A-2C in succession while preventing reverse rotation of the valve member 25. This can be accomplished by providing the valve 25 with a radial arm 25a which resiliently rises on ramps 23' inclined in the desired direction of rotation and forming stops for the valve in each position (see FIG. 4C). The device 23', 28' thus also forms a detent arrangement for holding the valve in each of the positions until the valve is rotated into the next position.

In all of these embodiments, the system operates essentially in the same manner. In the first step, after the vial has been mounted in the adaptor or thrust over the needle, the pressure inside the vial is equalized with sterile air (FIG. 2A), the air being drawn through the port 43 after having been sterilized by the filter 42. Atmospheric pressure is equalized with the pressure within the vial.

In the next step (FIG. 2B), communication between the vial 10 and the atmosphere outside of the connector is shutoff. Communication is established between the needle and the bag containing the IV solution.

By squeezing the IV container, some of the sterile air in the vial is forced into the container and some of the container liquid is forced into the vial. The vial is then shaken to dissolve the drug in the vial in the solution. By forcing air back into the vial, the reconstituted solution can be forced back into the IV container and this is accomplished by squeezing the container until all of the liquid in the vial has been transferred to the container and all of the air is now found in the vial.

The valve may now be rotated into the closed position (FIG. 2C) shutting-off the piercing member and vial from the liquid. This prevents IV solution from reentering the vial and diminishing the quantity which must be administered.

The embodiment of FIGS. 5A-5D operates in a similar manner. Here the valve is formed by a valve body 53 with respect to which a valve disk 52 can be rotated. The valve disk is provided with the piercing needle 50 whose passage 55 can register with a port 56 in the vent position illustrated in FIG. 5B. The port 56 communicates with the chamber 57 connected via a sterilizing air filter 59 with the atmosphere through a hole 60 in a cover 58 affixed to the valve body 53.

Upon rotation of the disk 52 to align the passage 55 with a port or passage 61 of a stem or tube connected to the IV container, the "mix" position is obtained (FIG. 5C).

In the final position, shown in FIG. 5D, corresponding to the closed position, the passage 55 is blocked and so too are the passages 56 and 61. The vial is applied to the needle 50 in the manner described.

I claim:

1. A method of preparing an aseptic solution for administration, comprising the steps of:
   (a) providing a flexible container containing a physiological diluent and having a wall with a valve formed with a piercing needle and a sterilizing filter communicating with the atmosphere;
   (b) fitting a medicament vial over said needle whereby said needle pierces a sealing membrane of said vial;
   (c) in a first position of said valve communicating between said filter and said vial and blocking communication of said container with said vial and said filter, admitting sterile air from the atmosphere through said filter into said vial to bring a pressure in said vial to atmospheric pressure;
   (d) thereafter in a second position of said valve communicating between said vial and said container and blocking communication of said vial and said container with said filter, squeezing said container at least once to displace diluent from said container into said vial and a mixture of diluent and said medicament from said vial into said container; and
   (e) thereafter forcing air from said container into said vial.

2. The method defined in claim 1, further comprising the step of:
   (f) subsequently displacing said valve into a third position in which communication between said vial and said filter and communication between said vial and said container are blocked.

3. The method defined in claim 2, further comprising the step of filtering liquid passed between said vial and said container in step (d).

4. The method defined in claim 3, further comprising the step of indexing said valve in each of said positions.

5. An apparatus for preparing an aseptic preparation for administration, comprising:
   a flexible container containing a physiological diluent;
   a valved connector in a wall of said container and including:
   a connector body formed with a piercing needle,
   a tubular stem insertable through said wall of said container, and
   means displaceable into a first position for connecting a port of said body to said needle, a second position for connecting said needle with said container and blocking communication with said port, and a third position blocking communication between said needle and said container and blocking communication between said port and said container;
   a sterile filter on said connector communicating between said port and the atmosphere; and
   a vial having a sealing membrane pierceable by said needle and adapted to be received by said connector over said needle, whereby in said first position of said valve said filter communicates with said vial and communication of said container with said vial and said filter is blocked, and sterile air from the atmosphere is admitted through said filter into said vial to bring a pressure in said vial to atmospheric pressure, thereafter in said second position of said valve said vial communicates with said container and communication of said vial and said container with said filter is blocked so that squeezing said container at least once displaces diluent from said container into said vial and a mixture of diluent and said medicament from said vial into said container, and in said third position, mixture from said container is prevented from reentering said vial.

6. The apparatus defined in claim 5 wherein said needle is provided with a removable protective cap.

7. The apparatus defined in claim 5, further comprising an adaptor mounted on said body, surrounding said needle and receiving said vial with a tight fit.

8. The apparatus defined in claim 5, further comprising cooperating indexing means on said body and said displaceable means for indexing said displaceable means in each of said positions.

9. The apparatus defined in claim 5, further comprising means constraining said displaceable means for movement only in one direction to allow said displaceable means to pass through said positions only in the sequence of first, second and third positions.

10. The apparatus defined in claim 5, further comprising a filter having a pore size between 0.2 and 200 micrometers interposed between said connector and said container and preventing particles from passing into said container.

11. The apparatus defined in claim 10 wherein said connector is provided with a skirt protecting a user against spillage and leakage.

12. A connector adapted to be attached to a flexible container containing a diluent for introducing a medicament into said container, said connector comprising:
a connector body;
a piercing needle on said body adapted to pierce a sealing membrane of a medicament vial;
means for connecting said connector body with said container;
a port formed in said body and a sterilizing filter connecting said port with the atmosphere; and
means on said body displaceable between a first position wherein said port is connected with said needle and communication between said port and said container is blocked, and a second position wherein said needle is connected with said container and communication with said port is blocked.

13. The connector defined in claim 12 wherein said displaceable means has a third position in which communication between said container and said vial and communication between said container and said port are blocked.

14. The connector defined in claim 13 wherein said needle is provided with a removable protective cap.

15. The connector defined in claim 13, further comprising an adaptor mounted on said body, surrounding said needle and receiving said vial with a tight fit.

16. The connector defined in claim 13, further comprising cooperating indexing means on said body and said displaceable means for indexing said displaceable means in each of said positions.

17. The connector defined in claim 13, further comprising means constraining said displaceable means for movement only in one direction to allow said displaceable means to pass through said positions only in the sequence of first, second and third positions.

18. The connector defined in claim 13, further comprising a filter having a pore size between 0.2 and 200 micrometers interposed between said connector and said container and preventing particles from passing into said container.

19. The connector defined in claim 18 wherein said connector is provided with a skirt protecting a user against spillage and leakage.

* * * * *